US008258116B2

(12) United States Patent
Kwong et al.

(10) Patent No.: US 8,258,116 B2
(45) Date of Patent: Sep. 4, 2012

(54) COMBINATION THERAPY FOR THE TREATMENT OF HCV INFECTION

(75) Inventors: Ann Kwong, Cambridge, MA (US); Nagraj Mani, Natick, MA (US); Yi Zhou, Lexington, MA (US); Chao Lin, Winchester, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 345 days.

(21) Appl. No.: 12/598,802

(22) PCT Filed: May 5, 2008

(86) PCT No.: PCT/US2008/005758
§ 371 (c)(1),
(2), (4) Date: Mar. 24, 2010

(87) PCT Pub. No.: WO2008/137126
PCT Pub. Date: Nov. 13, 2008

(65) Prior Publication Data
US 2010/0172866 A1     Jul. 8, 2010

Related U.S. Application Data

(60) Provisional application No. 60/927,581, filed on May 4, 2007, provisional application No. 60/931,425, filed on May 23, 2007.

(51) Int. Cl.
*A01N 43/04*     (2006.01)
*A61K 31/70*     (2006.01)
(52) U.S. Cl. .................. 514/49; 514/43; 514/50; 514/51
(58) Field of Classification Search .................. None
See application file for complete search history.

(56) References Cited

OTHER PUBLICATIONS

Mo et al. Antimicrobial Agents and Chemotherapy (2005), vol. 49, pp. 4305-4314.*
Giuliam et al. Xenobiotica (2005), vol. 35, pp. 1035-1054.*
Lin, C., et al., In Vitro Studies of Cross-resistance Mutations against Two Hepatitis C Virus Serine Protease Inhibitors, VX-950 and BILN 2061*, The Journal of Biological Chemistry, Nov. 4, 2005, pp. 36784-36791, vol. 280, No. 44, The American Society for Biochemistry and Molecular Biology, Inc., U.S.A.
McHutchison, J. G., et al., The face of future hepatitis C antiviral drug development: Recent biological and virologic advances and their translation to drug development and clinical practice, Journal of Hepatology, 2006, pp. 411-421, vol. 44, European Association for the Study of the Liver, Elsevier B.V.
Kadam, J. S., et. al., Changing Treatment Paradigms: Hepatitis C Virus in HIV-Infected Patients, AIDS Patient Care and STDs, 2007, pp. 154-168, vol. 21, No. 3, Mary Ann Liebert, Inc.
Khokhar, A. S., et al., Future Therapies for Hepatitis C, Hepatitis C: Current and Future Therapies, Current Hepatitis Reports, 2006, pp. 121-128, vol. 5, Current Science Inc.
Dusheiko, G., Hepatitis C, Medicine, Liver Infections, 2006, pp. 43-48, vol. 35:1, Elsevier Ltd.
Sulkowski, M., Specific Targeted Antiviral Therapy for Hepatitis C, Current Gastroenterology Reports, Liver, 2007, pp. 5-13, vol. 9, Current Medicine Group LLC.
Sheldon, J., et al., Novel Protease and polymerase inhibitors for the treatment of hepatitis C virus infection, Expert Opin. Investig. Drugs, 2007, pp. 1171-1181, vol. 16(8), Informa UK Ltd.
Revill, P., et al., Telaprevir, HCV NS3 Protease Inhibitor Treatment of Hepatitis C, Drugs of the Future, 2007, pp. 788-798, vol. 32(9), Prous Science.
McCown, M. F., et al., The HCV replicon presents a higher barrier to resistance to nucleoside analogs than to non-nucleoside polymerase or protease inhibitors, Antimicrob. Agents Chemother, 2008, pp. 1-36, American Society for Microbiology.

* cited by examiner

*Primary Examiner* — Patrick Lewis
(74) *Attorney, Agent, or Firm* — Honigman Miller Schwartz and Cohn LLP; Noel E. Day; Jonathan P. O'Brien

(57) ABSTRACT

The present invention relates to therapeutic combinations comprising a protease inhibitor and a polymerase inhibitor for the treatment of HCV. The present invention also relates to therapeutic combinations comprising VX-950 and a polymerase inhibitor. Also within the scope of the invention are methods using the therapeutic combinations of the present invention for treating HCV infection or alleviating one or more symptoms thereof in a patient. The present invention also provides kits comprising the combinations of the present invention.

15 Claims, No Drawings

COMBINATION THERAPY FOR THE TREATMENT OF HCV INFECTION

CROSS REFERENCE TO RELATED APPLICATION

This application is the U.S. National phase of PCT Application No. PCT/US2008/005758 filed on May 5, 2008, which claims priority to U.S. Provisional Application Nos. 60/927,581, filed May 4, 2007, and 60/931,425, filed May 23, 2007, the contents of which are incorporated herein by reference in their entireties.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," J. Hepatology, 31., (Suppl. 1), pp. 17-24 (1999)]. Nearly four million individuals may be infected in the United States alone [M. J. Alter et al., "The Epidemiology of Viral Hepatitis in the United States," Gastroenterol. Clin. North Am., 23, pp. 437-455 (1994); M. J. Alter "Hepatitis C Virus Infection in the United States," J. Hepatology, 31, (Suppl. 1), pp. 88-91 (1999)].

Upon first exposure to HCV only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," FEMS Microbiology Reviews, 14, pp. 201-204 (1994); D. Lavanchy, "Global Surveillance and Control of Hepatitis C," J. Viral Hepatitis, 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", FEMS Microbiology Reviews, 14, pp. 211-220 (1994); I. Saito et. al., "Hepatitis C Virus Infection is Associated with the Development of Hepatocellular Carcinoma," Proc. Natl. Acad. Sci. USA, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et. al., "Genetic Organization and Diversity of the Hepatitis C Virus," Proc. Natl. Acad. Sci. USA, 88, pp. 2451-2455 (1991); N. Kato et al., "Molecular Cloning of the Human Hepatitis C Virus Genome From Japanese Patients with Non-A, Non-B Hepatitis," Proc. Natl. Acad. Sci. USA, 87, pp. 9524-9528 (1990); A. Takamizawa et. al., "Structure and Organization of the Hepatitis C Virus Genome Isolated From Human Carriers," J. Virol., 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," J. Virol., 67, pp. 3835-3844 (1993); A. Grakoui et. al., "Characterization of the Hepatitis C Virus-Encoded Serine Proteinase: Determination of Proteinase-Dependent Polyprotein Cleavage Sites," J. Virol., 67, pp. 2832-2843 (1993); A. Grakoui et. al., "Expression and Identification of Hepatitis C Virus Polyprotein Cleavage Products," J. Virol., 67, pp. 1385-1395 (1993); L. Tomei et. al., "NS3 is a serine protease required for processing of hepatitis C virus polyprotein", J. Virol., 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decrease viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein," Proc. Natl. Acad. Sci. USA, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", J. Virol., 68, pp. 8147-8157 (1994)].

The HCV NS3 serine protease and its associated cofactor, NS4A, help process all of the viral enzymes, and are thus considered essential for viral replication. This processing appears to be analogous to that carried out by the human immunodeficiency virus aspartyl protease, which is also involved in viral enzyme processing. HIV protease inhibitors, which inhibit viral protein processing, are potent antiviral agents in man indicating that interrupting this stage of the viral life cycle results in therapeutically active agents. Consequently HCV NS3 serine protease is also an attractive target for drug discovery.

Until recently, the only established therapy for HCV disease was interferon treatment. However, interferons have significant side effects [M. A. Wlaker et al., "Hepatitis C Virus: An Overview of Current Approaches and Progress," DDT, 4, pp. 518-29 (1999); D. Moradpour et al., "Current and Evolving Therapies for Hepatitis C," Eur. J. Gastroenterol. Hepatol., 11, pp. 1199-1202 (1999); H. L. A. Janssen et al. "Suicide Associated with Alfa-Interferon Therapy for Chronic Viral Hepatitis," J. Hepatol., 21, pp. 241-243 (1994); P. F. Renault et al., "Side Effects of Alpha Interferon," Seminars in Liver Disease, 9, pp. 273-277 (1989)] and induce long term remission in only a fraction (~25%) of cases [O. Weiland, "Interferon Therapy in Chronic Hepatitis C Virus Infection", FEMS Microbiol. Rev., 14, pp. 279-288 (1994)]. Recent introductions of the pegylated forms of interferon (PEG-INTRON® and PEGASYS®) and the combination therapy of ribavirin and pegylated interferon (REBETROL®) have resulted in only modest improvements in remission rates and only partial reduction of side effects. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

SUMMARY OF THE INVENTION

This invention relates to therapeutic combinations comprising VX-950 and a polymerase inhibitor.

The invention also relates to methods of treating HCV infection or alleviating one or more symptoms thereof in a patient, comprising administering to said patient a therapeutic combination of the present invention.

It is yet another object of the present invention to provide a pharmaceutical regimen for treating HCV infection in a patient.

DETAILED DESCRIPTION OF THE INVENTION

Definitions

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, or as exemplified by particular classes, subclasses, and species of the invention.

As used herein, "patient" refers to a mammal, including a human.

The term "polymerase inhibitor," as used herein, refers to compounds that inhibit the activity of HCV RNA dependent RNA polymerase (RdRp). Polymerase inhibitors of the following invention include, but are not limited to, the compounds of formula I, II and III. The polymerase inhibitor can be a nucleoside or non-nucleoside inhibitor. A nucleoside polymerase inhibitor binds to the substrate of the enzyme; whereas, the polymerase non-nucleoside binds to different site while still inhibiting the enzyme, e.g., an allosteric inhibitor.

The term "protease inhibitor," as used herein refers to means an agent (compound or biological) that is effective to inhibit the function of HCV NS3 protease in a mammal. Protease inhibitors of the following invention include, but are not limited to, VX-950.

As used herein, "VX-950" refers to an HCV inhibitor shown below and described in PCT Publication Number WO 02/18369, which is incorporated herein by reference in its entirety.

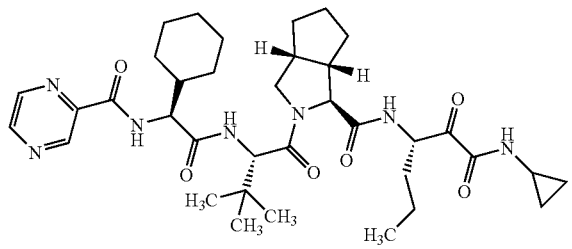

The term "therapeutic combination" as used herein means a combination of one or more active drug substances, i.e., compounds having a therapeutic utility. Typically, each such compound in the therapeutic combinations of the present invention will be present in a pharmaceutical composition comprising that compound and a pharmaceutically acceptable carrier. The compounds in a therapeutic combination of the present invention may be administered simultaneously or separately, as part of a regimen.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays.

Therapeutic Combinations

The present invention relates to therapeutic combinations comprising a protease inhibitor and a polymerase inhibitor for the treatment of HCV.

Protease Inhibitors

In one aspect of the invention, the protease inhibitor is VX-950.

VX-950, an HCV inhibitor with its structure shown below is such a compound in need. VX-950 is described in PCT Publication Number WO 02/18369, which is incorporated herein by reference in its entirety.

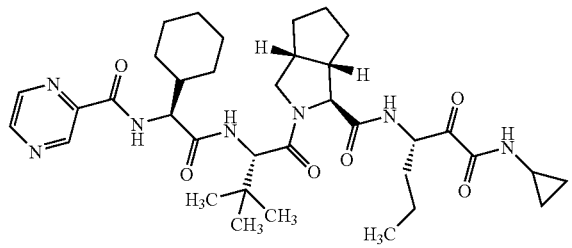

VX-950, a potent and specific NS3-4A protease inhibitor demonstrated substantial antiviral activity in a phase 1b trial of subjects infected with HCV genotype 1 (Study VX04-950-101). The degree to which a subject responds to treatment and the rate at which viral rebound is observed could in part be due to genotypic differences in sensitivity to the protease inhibitor. The rapid replication rate of HCV, along with the poor fidelity of its polymerase, gives rise to an accumulation of mutations throughout its genome [P. Simmonds, "Genetic diversity and evolution of hepatitis C virus—15 years on," J. Gen. Virol., 85, pp. 3173-88 (2004)]. The degree to which sequence variability in the protease region affects the catalytic efficiency of the enzyme or the binding of an inhibitor is not known. Additionally, the generation of numerous viral genomes with remarkable sequence variation presents potential problems of emerging drug resistant virus in subjects treated with antiviral therapy. Indeed, drug resistance against antiviral drugs, such as HIV protease inhibitors, is well documented [Johnson et al., Top. HIV Med., 12, pp. 119-24 (2004)]. Drug resistant mutations have already been shown to develop in vitro in the presence of HCV protease inhibitors [Lin et al., "In vitro studies of cross-resistance mutations against two hepatitis C virus serine protease inhibitors, VX-950 and BILN 2061," J. Biol. Chem., 280, pp. 36784-36791 (2005), which is incorporated herein by reference in its entirety; Lin et al., "In vitro resistance studies of hepatitis C virus serine protease inhibitors, VX-950 and BILN 2061: Structural analysis indicates different resistance mechanisms," J. Biol. Chem., 279, pp. 17508-17514 (2004), which is incorporated herein by reference in its entirety; Lu et al., Antimicrob. Agents Chemother., 48, pp. 2260-6 (2004); Trozzi et al., "In vitro selection and characterization of hepatitis C virus serine protease variants resistant to an active-site peptide inhibitor," J. Virol. 77, pp. 3669-79 (2003)]. Mutations resistant to the protease inhibitor BILN 2061 have been found at positions R155Q, A156T, and D168V/A/Y in the NS3 gene, but no mutations have yet been observed in the NS4 region or in the protease cleavage sites. A VX-950 resistance mutation has also been found in vitro at position A156S. Cross-resistant mutations against both VX-950 and BILN 2061 have also been shown to develop in vitro at position 156 (A156V/T)(Lin et al., 2005, supra).

In other embodiments, the protease inhibitor is described in international patent application publication number WO2007/025307, the entire contents of which is incorporated herein.

In still other embodiments, the protease inhibitor is described in one or more of the following publications: WO1997/43310, US20020016294, WO2001/81325, WO2002/08198, WO2001/77113, WO2002/08187, WO2002/08256, WO2002/08244, WO2003/006490, WO2001/74768, WO1999/50230, WO1998/17679, WO2002/48157, US20020177725, WO2002/060926, US20030008828, WO2002/48116, WO2001/64678, WO2001/07407, WO1998/46630, WO2000/59929, WO1999/07733, WO2000/09588, US20020016442, WO2000/09543, WO1999/07734, U.S. Pat. No. 6,018,020, U.S. Pat. No. 6,265,380, U.S. Pat. No. 6,608,027, US20020032175, US20050080017, WO1998/22496, U.S. Pat. No. 5,866,684, WO2002/079234, WO2000/31129, WO1999/38888, WO1999/64442, WO2004/072243, and WO2002/18369, the contents of all of which are incorporated herein by reference in their entireties.

Polymerase Inhibitors

The polymerase inhibitors can be a nucleoside or a non-nucleoside inhibitor.

In an embodiment of the first aspect, the polymerase inhibitor is the compound of formula (I)

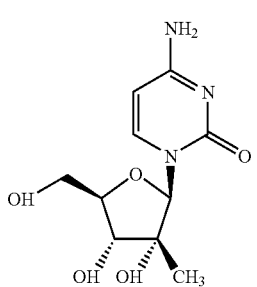

(I)

or a pharmaceutically acceptable salt thereof.

In another embodiment of the first aspect, the polymerase inhibitor is the compound of formula (II)

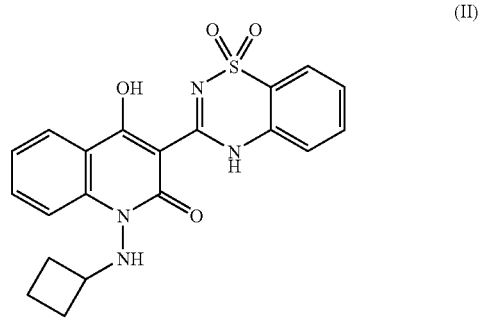

(II)

or a pharmaceutically acceptable salt thereof.

In another embodiment of the first aspect, the polymerase inhibitor is the compound of formula (III)

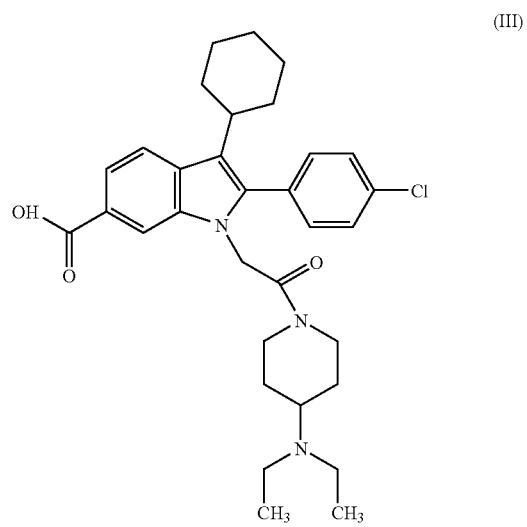

(III)

or a pharmaceutically acceptable salt thereof.

In another aspect, the invention provides a therapeutic combination of VX-950 and the polymerase inhibitor of compound (I)

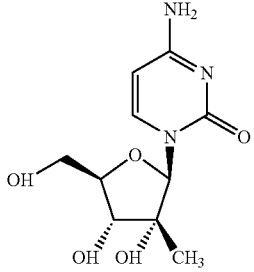

(I)

or a pharmaceutically acceptable salt thereof.

In another aspect, the invention provides a therapeutic combination of VX-950 and the polymerase inhibitor of compound (II)

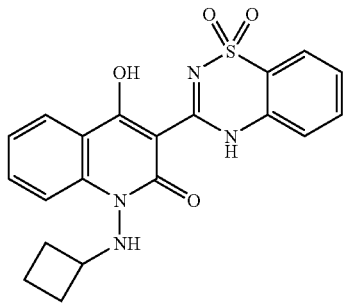

(II)

or a pharmaceutically acceptable salt thereof.

In another aspect, the invention provides a therapeutic combination of VX-950 and the polymerase inhibitor of compound (III)

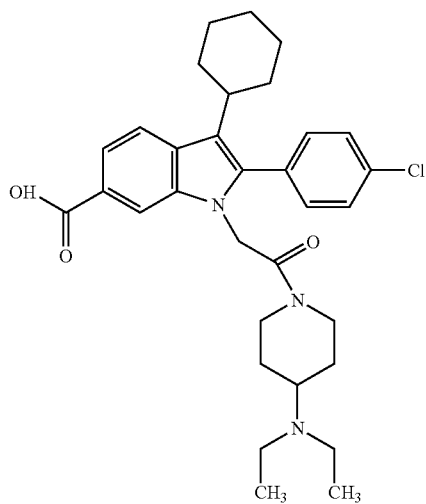

(III)

or a pharmaceutically acceptable salt thereof.

In other embodiments, the polymerase inhibitor is selected from the inhibitors known in the art. For instance, the polymerase inhibitor is described in one or more of the following international patent application publications: WO2008/011337; WO2006/093801; WO2005/019191; WO2004/041818; WO2007/150001; WO2006/066079; WO2006/137706; WO2006/011719; WO2004/108719; WO2004/108068; WO2004/033450; WO2003/084953; WO2008/019477; WO2007/019674; WO2006/007693; WO2005/080388; WO2004/065367; WO2004/064925; WO2003/010141; WO2003/010140; WO2003/007945; WO2002/004425; WO2008/021928; WO2008/021927; WO2007/143521; WO2006/020082; WO2004/014852; WO2004/014313; WO2003/026587; WO2003/002518; WO2002/079187; WO2008/011521; WO2008/008912; WO2006/138744; WO2007/039144; WO2006/045613; WO2006/045615; WO2005/103045; WO2005/092863; WO2005/079799; WO2004/076415; WO2004/037818; WO2004/009543; WO2003/037894; WO2003/037893; WO2007/082554; WO2007/028789; WO2006/119975; WO2006/046030; WO2006/046039; WO2006/029912; WO2006/027628; WO2006/008556; WO2005/034941; WO2004/087714; WO2003/062211; WO2002/006246; WO2006/052013; WO2005/080399; WO2005/049622; WO2005/014543; WO2003/000254; WO2007/023381; WO2006/018725; WO2004/074270; WO2004/073599; WO2003/082848; WO2004/002977; WO2004/002944; WO2004/002940; WO2006/117306; WO2006/050035; WO2002/100851; WO2007/147794; WO2007/088148; WO2007/071434; WO2006/100106; WO2006/119646; WO2005/112640; WO2004/052885; WO2004/052879; WO2004/041201; WO2007/092558; WO2005/016932; WO2004/091724; WO2003/099824; WO2003/099275; WO2008/009078; WO2007/034127; WO2007/041632; WO2007/005779; WO2007/002639; WO2006/065590; WO2006/019831; WO2004/080453; WO2003/101993; WO2003/082265; WO2001/077091; and WO1994/12192. The entire content of each of the foregoing publications is incorporated herein in its entirety.

In other examples, the polymerase inhibitor is described in one or more of the following U.S. patent application publications: US2004167123; US2004162285; US20040097492; US20040087577; US20070275947; US20070275930; US20070270406; US20070270405; US2005075376; US20070032488; US20030050320; US2005154056; US2006040927; US2006094706; US2006258682; US2006223834; US2006217390; US2006019976; US2005107364; US2006183751; US2006063821; and US2005176701. The entire content of each of the foregoing publications is incorporated herein in its entirety.

In still further examples, the polymerase inhibitor is described in U.S. Pat. No. 7,112,600 or European Patent No. EP 1321463. The entire content of each of the foregoing publications is incorporated herein.

In still further embodiments, the polymerase inhibitor is selected from A-837093, being developed by Abbott Laboratories; GS-9190, being developed by Gilead Sciences; PF-868 and PF-554, being developed by Pfizer; R1479, R1626 (prodrug of R1479), R7128, and R1728, being developed by Roche Pharmaceuticals; PST 7081, being developed by Pharmasset and Roche Pharmaceuticals; IDX102, IDX184, NM107, NM283 (prodrug of NM107) called Valopicitabine, being developed by Idenix; and VCH-916 and VCH-759, being developed by ViroChem; and HCV-796, being developed by Wyeth. Other polymerase inhibitors are in development by Genelabs; Boehringer Ingelheim; Anadys; Celera; Schering; and Medavir.

According to another aspect, the present invention provides kits for use in treating HCV infection in a patient. The kits of the present invention comprise any one of the therapeutic combinations of the present invention. The kits further comprise instructions for utilizing the therapeutic combinations. The kits may be tailored to the needs of classes or types of patients or other clinically relevant factors such as age, body weight, concomitant diseases/conditions, severity and stage of HCV infection, responsiveness or non-responsiveness to prior treatments, propensity for side effects, etc. For example, the therapeutic combination in a kit may be tailored for dosages suitable for patients having a body weight of, e.g., 75 kg. Or, the therapeutic combination in a kit may be tailored for dosages suitable for patients having a body weight of, e.g., less than or equal to 75 kg. Or, the therapeutic combination in a kit may be tailored for pediatric use, wherein the dosage for children is varied depending on factors such as age, body weight, severity of disease, etc.

According to another aspect, the present invention provides a kit comprising: (i) a plurality of VX-950 compositions; (ii) a plurality of polymerase inhibitor compositions; and (iii) instructions for utilizing the above compositions.

In another aspect, the invention provides methods of using the therapeutic combinations of the present invention for treating HCV infection or alleviating one or more symptoms thereof in a patient.

In one embodiment, the HCV infection is genotype.

In another embodiment, the patient is a treatment naïve patient.

In another embodiment, the patient is non-reponsive to interferon monotherapy.

In another embodiment, the patient is non-reponsive to combination therapy using ribaviron and an interferon.

In another aspect, the invention provides a method of reducing HCV-RNA levels in a patient in need thereof, comprising the step of administering to said patient a therapeutic combination of the present invention.

In an embodiment of the invention, the HCV-RNA levels in the patient are reduced to a less than detectable level.

In another aspect, the invention provides a pharmaceutical regimen comprising administering to a patient in need thereof a therapeutic combination of the present invention until the HCV-RNA level in the patient is below a detectable level.

Formulations, Administrations, and Uses

If pharmaceutically acceptable salts of the compounds of this invention are utilized in the therapeutic combinations, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2 hydroxyethanesulfonate, lactate, maleate, methanesulfonate, 2 naphthalenesulfonate, nicotinate, oxalate, pamoate, pectinate, persulfate, 3 phenyl propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N methyl D glucamine, and salts with amino acids such as arginine, lysine, and so forth.

Also, the basic nitrogen containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose based substances, polyethylene glycol, sodium carboxymethylcellulose, polyacrylates, waxes, polyethylene polyoxypropylene block polymers, polyethylene glycol and wool fat.

The therapeutic combinations of this invention are formulated for pharmaceutical administration to a mammal. In one embodiment said mammal is a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra articular, intra synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In one embodiment, dosage levels of between about 0.01 and about 100 mg/kg body weight per day of VX-950 are useful in a combination therapy for the prevention and treatment of antiviral, particularly anti-HCV mediated disease. In another embodiment, dosage levels of between about 0.5 and about 75 mg/kg body weight per day of VX-950 are useful in a combination therapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). In one embodiment, such preparations contain from about 20% to about 80% active compound.

In one embodiment, dosage levels of between about 0.01 and about 100 mg/kg body weight per day of the polymerase inhibitor compounds described herein are useful in a combination for the prevention and treatment of antiviral, particularly anti-HCV mediated disease. In another embodiment, dosage levels of between about 0.5 and about 75 mg/kg body weight per day of the polymerase inhibitor compounds described herein are useful in a combination therapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). In one embodiment, such preparations contain from about 20% to about 80% active compound.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The therapeutic combination of this invention may additionally comprise another anti-viral agent, preferably an anti-HCV agent. Such anti-viral agents include, but are not limited to, immunomodulatory agents, such as alpha, beta, and gamma-interferons, pegylated derivatized interferon-alpha compounds, and thymosin; other anti-viral agents, such as ribavirin, amantadine, and telbivudine; other inhibitors of hepatitis C proteases (NS2—NS3 inhibitors and NS3—NS4A inhibitors); inhibitors of other targets in the HCV life cycle, including helicase and other polymerase inhibitors; inhibitors of internal ribosome entry; broad-spectrum viral inhibitors, such as IMPDH inhibitors (e.g., compounds of U.S. Pat. Nos. 5,807,876, 6,498,178, 6,344,465, 6,054,472, WO 97/40028, WO 98/40381, WO 00/56331, and mycophenolic acid and derivatives thereof, and including, but not limited to VX-497, VX-148, and/or VX-944); or combinations of any of the above. See also W. Markland et al., Antimicrobial & Antiviral Chemotherapy, 44, p. 859 (2000) and U.S. Pat. No. 6,541,496.

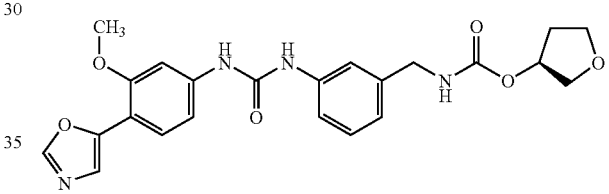

According to another aspect, the present invention provides a method of treating HCV infection or alleviating one or more symptoms thereof, in a patient, comprising administering a composition comprising a polymerase inhibitor of Formula I, II or III. In one embodiment, the patient is infected by an HCV variant. In another embodiment, the composition further comprises VX-950.

According to another aspect, the present invention provides a method of treating HCV infection or alleviating one or more symptoms thereof, in a patient, comprising administering a composition comprising a polymerase inhibitor of Formula I, II, or III, and VX-950. In one embodiment, the patient is infected by an HCV variant.

According to another aspect, the present invention provides a method of eliminating or reducing HCV infection in a cell, comprising administering a composition comprising a polymerase inhibitor of Formula I, II or III. In one embodiment, the cell contains an HCV variant. In another embodiment, the composition further comprises VX-950.

According to another aspect, the present invention provides a method of eliminating or reducing HCV infection in a cell, comprising administering a composition comprising a polymerase inhibitor of Formula I, II or III and VX-950. In one embodiment, the cell contains an HCV variant.

The following definitions are used herein (with trademarks referring to products available as of this application's filing date):

"Peg-Intron" means PEG-INTRON®, peginteferon alfa-2b, available from Schering Corporation, Kenilworth, N.J.;

"Intron" means INTRON-A®, interferon alfa-2b available from Schering Corporation, Kenilworth, N.J.;

"ribavirin" means ribavirin 1-beta-D-ribofuranosyl-1H-1,2,4-triazole-3-carboxamide, available from ICN Pharmaceuticals, Inc., Costa Mesa, Calif.; described in the Merck Index, entry 8365, Twelfth Edition; also available as REBETROL® from Schering Corporation, Kenilworth, N.J., or as COPEGASUS® from Hoffmann-La Roche, Nutley, N.J.;

"Pegasys" means PEGASYS®, peginterferon alfa-2a available Hoffmann-La Roche, Nutley, N.J.;

"Roferon" mean ROFERON®, recombinant interferon alfa-2a available from Hoffmann-La Roche, Nutley, N.J.;

"Berefor" means BEREFOR®, interferon alfa 2 available from Boehringer Ingelheim Pharmaceutical, Inc., Ridgefield, Conn.;

SUMIFERON®, a purified blend of natural alpha interferons such as Sumiferon available from Sumitomo, Japan;

WELLFERON®, interferon alpha n1 available from Glaxo Wellcome LTd., Great Britain; and ALFERON®, a mixture of natural alpha interferons made by Interferon Sciences, and available from Purdue Frederick Co., CT.

The term "interferon" as used herein means a member of a family of highly homologous species-specific proteins that inhibit viral replication and cellular proliferation, and modulate immune response, such as interferon alpha, interferon beta, or interferon gamma. The Merck Index, entry 5015, Twelfth Edition.

The therapeutic combination of the present invention may utilize natural alpha interferon 2a. Or, the therapeutic combination of the present invention may utilize natural alpha interferon 2b. The therapeutic combination of the present invention may utilize recombinant alpha interferon 2a or 2b. Additionally, the invention may utilize pegylated alpha interferon 2a or 2b. Interferons suitable for the present invention include:

(a) INTRON-A® (interferon-alpha 2B, Schering Plough),
(b) PEG-INTRON®,
(c) PEGASYS®,
(d) ROFERON®,
(e) BEREFOR®,
(f) SUMIFERON®,
(g) WELLFERON®,
(h) consensus alpha interferon available from Amgen, Inc., Newbury Park, Calif.,
(i) ALFERON®;
(j) VIRAFERON®;
(k) INFERGEN®; and
(l) ALBUFERON™.

As is recognized by skilled practitioners, protease and polymerase inhibitors would be preferably administered orally. Interferon is not typically administered orally. Nevertheless, nothing herein limits the methods or combinations of this invention to any specific dosage forms or regime. Thus, each component of a combination according to this invention may be administered separately, together, or in any combination thereof.

In one embodiment, the protease inhibitor and polymerase inhibitor are administered in separate dosage forms. In one embodiment, any additional agent is administered as part of a single dosage form with the protease inhibitor or as a separate dosage form. As this invention involves a combination of compounds, the specific amounts of each compound may be dependent on the specific amounts of each other compound in the combination. As recognized by skilled practitioners, dosages of interferon are typically measured in IU (e.g., about 4 million IU to about 12 million IU).

Accordingly, agents (whether acting as an immunomodulatory agent or otherwise) that may be used in combination with a compound of this invention include, but are not limited to, Albuferon™ (albumin-Interferon alpha) available from Human Genome Sciences; PEG-INTRON® (peginterferon alfa-2b, available from Schering Corporation, Kenilworth, N.J.); INTRON-A®, (interferon alfa-2b available from Schering Corporation, Kenilworth, N.J.); ribavirin 1-beta-D-ribofuranosyl-1H-1,2,4-triazole-3-carboxamide, available from ICN Pharmaceuticals, Inc., Costa Mesa, Calif.; described in the Merck Index, entry 8365, Twelfth Edition); REBETROL® (Schering Corporation, Kenilworth, N.J.), COPEGUS® (Hoffmann-La Roche, Nutley, N.J.); PEGASYS® (peginterferon alfa-2a available Hoffmann-La Roche, Nutley, N.J.); ROFERON® (recombinant interferon alfa-2a available from Hoffmann-La Roche, Nutley, N.J.); BEREFOR® (interferon alfa 2 available from Boehringer Ingelheim Pharmaceutical, Inc., Ridgefield, Conn.); SUMIFERON® (a purified blend of natural alpha interferons such as Sumiferon available from Sumitomo, Japan); WELLFERON® (interferon alpha n1 available from Glaxo Wellcome Ltd., Great Britain); ALFERON® (a mixture of natural alpha interferons made by Interferon Sciences, and available from Purdue Frederick Co., CT); alpha-interferon; natural alpha interferon 2a; natural alpha interferon 2b; pegylated alpha interferon 2a or 2b; consensus alpha interferon (Amgen, Inc., Newbury Park, Calif.); VIRAFERON®; INFERGEN®; REBETRON® (Schering Plough, Interferon-alpha 2B+Ribavirin); pegylated interferon alpha (Reddy, K. R. et al. "Efficacy and Safety of Pegylated (40-kd) Interferon alpha-2a Compared with Interferon alpha-2a in Noncirrhotic Patients with Chronic Hepatitis C (Hepatology, 33, pp. 433-438 (2001); consensus interferon (Kao J. H., et al., "Efficacy of Consensus Interferon in the Treatment of Chronic Hepatitis," J. Gastroenterol. Hepatol., 15, pp. 1418-1423 (2000); lymphoblastoid or "natural" interferon; interferon tau (Clayette, P. et al., "IFN-tau, A New Interferon Type I with Antiretroviral activity," Pathol. Biol., (Paris) 47, pp. 553-559 (1999); interleukin-2 (Davis, G. L. et al., "Future Options for the Management of Hepatitis C," Seminars in Liver Disease, 19, pp. 103-112 (1999); Interleukin-6 (Davis et al. "Future Options for the Management of Hepatitis C," Seminars in Liver Disease, 19, pp. 103-112 (1999); interleukin-12 (Davis, G. L. et al., "Future Options for the Management of Hepatitis C," Seminars in Liver Disease, 19, pp. 103-112 (1999); and compounds that enhance the development of type 1 helper T cell response (Davis et al., "Future Options for the Management of Hepatitis C," Seminars in Liver Disease, 19, pp. 103-112 (1999)). Also included are compounds that stimulate the synthesis of interferon in cells (Tazulakhova, E. B. et al., "Russian Experience in Screening, analysis, and Clinical Application of Novel Interferon Inducers," J. Interferon Cytokine Res., 21 pp. 65-73) including, but are not limited to, double stranded RNA, alone or in combination with tobramycin, and Imiquimod (3M Pharmaceuticals; Sauder, D. N. "Immunomodulatory and Pharmacologic Properties of Imiquimod," J. Am. Acad. Dermatol., 43 pp. S6-11 (2000)).

Compounds that stimulate the synthesis of interferon in cells (Tazulakhova, E. B. et al., "Russian Experience in Screening, analysis, and Clinical Application of Novel Interferon Inducers," J. Interferon Cytokine Res., 21, pp. 65-73) include, but are not limited to, double stranded RNA, alone or in combination with tobramycin, and Imiquimod (3M Pharmaceuticals; Sauder, D. N. "Immunomodulatory and Pharmacologic Properties of Imiquimod," J. Am. Acad. Dermatol., 43 pp. S6-11 (2000)).

Other non-immunomodulatory or immunomodulatory compounds may be used in combination with a compound of this invention including, but not limited to, those specified in WO 02/18369, which is incorporated herein by reference (see, e.g., page 273, lines 9-22 and page 274, line 4 to page 276, line 11).

This invention may also involve administering a cytochrome P450 monooxygenase inhibitor. CYP inhibitors may be useful in increasing liver concentrations and/or increasing blood levels of compounds that are inhibited by CYP.

If an embodiment of this invention involves a CYP inhibitor, any CYP inhibitor that improves the pharmacokinetics of the relevant NS3/4A protease may be used in a method of this invention. These CYP inhibitors include, but are not limited to, ritonavir (WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methyl pyrazole, cyclosporin, and clomethiazole. For preferred dosage forms of ritonavir, see U.S. Pat. No. 6,037,157, and the documents cited therein: U.S. Pat. No. 5,484,801, U.S. patent application Ser. No. 08/402,690, and International Applications WO 95/07696 and WO 95/09614).

Methods for measuring the ability of a compound to inhibit cytochrome P450 monooxygenase activity are known (see U.S. Pat. No. 6,037,157, and Yun et al., Drug Metabolism & Disposition, 21, pp. 403-407 (1993).

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

The invention provides a method for treating a patient infected with a virus characterized by a virally encoded serine protease that is necessary for the life cycle of the virus by administering to said patient a pharmaceutically acceptable composition of this invention. In one embodiment, the methods of this invention are used to treat a patient suffering from an HCV infection. Such treatment may completely eradicate the viral infection or reduce the severity thereof. In another embodiment, the patient is a human being.

The methods of this invention may additionally comprise the step of administering to said patient an anti-viral agent, preferably an anti-HCV agent. Such anti-viral agents include, but are not limited to, immunomodulatory agents, such as alpha-, beta-, and gamma-interferons, pegylated derivatized interferon-α compounds, and thymosin; other anti-viral agents, such as ribavirin, amantadine, and telbivudine; other inhibitors of hepatitis C proteases (NS2—NS3 inhibitors and NS3—NS4A inhibitors); inhibitors of other targets in the HCV life cycle, including but not limited to helicase and other polymerase inhibitors; inhibitors of internal ribosome entry; broad-spectrum viral inhibitors, such as IMPDH inhibitors (e.g., VX-497 and other IMPDH inhibitors disclosed in U.S. Pat. Nos. 5,807,876 and 6,498,178, mycophenolic acid and derivatives thereof); inhibitors of cytochrome P-450, such as ritonavir, or combinations of any of the above.

Such additional agent may be administered to said patient as part of a single dosage form comprising both a compound of this invention and an additional anti-viral agent. Alternatively, the additional agent may be administered separately from the compound of this invention, as part of a multiple dosage form, wherein said additional agent is administered prior to, together with or following a composition comprising a compound of this invention.

The present invention may also be utilized as a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

The invention may also be utilized as a method of treating materials that may potentially come into contact with a virus characterized by a virally encoded serine protease necessary for its life cycle. This method comprises the step of contacting said material with a compound according to the invention. Such materials include, but are not limited to, surgical instruments and garments (e.g. clothes, gloves, aprons, gowns, masks, eyeglasses, footwear, etc.); laboratory instruments and garments (e.g. clothes, gloves, aprons, gowns, masks, eyeglasses, footwear, etc.); blood collection apparatuses and materials; and invasive devices, such as, for example, shunts and stents.

All references cited within this document are incorporated herein by reference.

PREPARATIONS AND EXAMPLES

In order that the invention described herein may be more fully understood, the following examples are set forth. It should be understood that these examples are for illustrative purposes only and are not to be construed as limiting this invention in any manner.

Assays for Detecting and Measuring Inhibition Properties of Compounds

A. HCV Replicon Cells

Huh-7 cells were propagated in Dulbecco's modified Eagle's medium (DMEM, JRH Biosciences, Lenexa, Kans.) supplemented with 10% heat-inactivated FBS (fetal bovine serum), 2 mM L-glutamine, and nonessential amino acids (JRH). The cells were transfected with an in vitro transcribed HCV replicon RNA identical to replicon 1377neo/NS3-3'/wt as described by Lohmann et al. (1999). Stable cell clones were selected and maintained in the presence of 250 μg/mL G418 (Invitrogen, Carlsbad, Calif.). One of the clones, 24-2, was used as the wild-type in the subsequent HCV replicon assays for combination studies. The HCV NS3 protease variant replicons were constructed in the background of the mADE wild-type replicon as described previously [Chao Lin et al., "In Vitro Resistance Studies of Hepatitis C Virus Serine Protease Inhibitors, VX-950 and BILN 2061: Structural Analysis Indicates Different Resistance Mechanisms," Journal of Biological Chemistry, 279(17); pp. 17508-17514 (2004)]. The replicon cells were propagated in DMEM supplemented with 10% FBS, 2 mM L-glutamine, nonessential amino acids, and 250 µg/mL G418. The cells were split twice per week in fresh media upon reaching confluence. There are approximately 200-300 copies of HCV RNA per 24-2 replicon cell.

HCV replicon RNA from cells was measured using the Quantigene Discover XL kit (Panomics Inc., Fremont Calif.) as per the manufacturer's instructions. Briefly, compound-treated replicon cells were lysed and immobilized on to capture plates using HCV specific oligonucleotides (designed based on the 5' UTR region of HCV 1b genome sequence AJ238799 in the GenBank database) over night and the relative amounts of captured RNA was measured using oligonucleotide probe sets as per the manufacturer's instructions.

B. 2-Day HCV Replicon $IC_{50}$ Assay

On the day prior to the assay, 10,000 replicon cells were plated per well of a 96-well plate and allowed to attach and grow overnight in DMEM (Invitrogen, Carlsbad, Calif.) supplemented with 10% heat-inactivated FBS (JRH Biosciences, Lenexa, Kans.), 2 mM L-glutamine (Invitrogen), nonessential amino acids (Invitrogen) and 250 µg/ml G418 (Invitrogen). Next day, the medium was removed and antiviral agents that were serially diluted in DMEM containing 2% FBS and 0.5% DMSO (Sigma Chemical Co., St. Louis, Mo.) without G418, was added. The replicon cells were incubated with the antiviral agents for 48 h. HCV replicon RNA from cells was measured using the Quantigene Discover XL kit (Panomics Inc., Fremont Calif.) as per the manufacturer's instructions. Briefly, compound-treated replicon cells were lysed and immobilized onto capture plates using HCV specific oligonucleotides overnight and the relative amounts of captured RNA was measured using oligonucleotide probe sets as per the manufacturer's instructions. Unless indicated otherwise, each data point represents the average of three replicates. The $IC_{50}$ is the concentration of the compound at which the HCV replicon RNA level in cells is reduced by 50% as compared to the untreated replicon cell controls. To monitor the effect of compounds on cell proliferation or cell viability, replicon cells were treated with serially diluted compounds for 48 h, after which cell viability was determined using a CellTiter Glo assay (Promega, Madison, Wis.). Each $CC_{50}$ is derived from at least two replicates and is the concentration of the compound at which the number of viable cells is reduced by 50% as compared to untreated cell controls. The $IC_{50}$ and $CC_{50}$ was determined using 4-parameter curve fitting in the SoftMax Pro program (Molecular Devices, Sunnyvale, Calif.).

C. Synergy and Antagonism Analysis

The effects of drug-drug combinations were evaluated using the Bliss independence model [W. R. Greco et al., "The search for synergy: a critical review from a response surface perspective," Pharmacol. Rev., 47, pp. 331-385 (1995)]. The experimental data were analyzed by using MacSynergy, a three-dimensional analytical method developed by Prichard and Shipman [M. N. Prichard and C. Shipman, Jr., "A three-dimensional model to analyze drug-drug interactions," Antivir. Res., 14, pp. 181-205 (1990)]. In this model, the theoretical additive effect is calculated from the dose-response curves of individual compounds by the equation $Z=X+Y(1-X)$, where X and Y represent the inhibition produced by drug 1 alone and drug 2 alone, respectively, and Z represents the effect produced by the combination of drug 1 and drug 2. The theoretical additive surface is subtracted from the actual experimental surface, resulting in a surface that would appear as a horizontal plane at 0% inhibition if the combination were merely additive. Any peak above this plane would indicate synergy, whereas any depression below it would indicate antagonism. The 95% confidence intervals for the experimental dose-response surface are used to evaluate the data statistically. The volume of the peak or depression is calculated to quantify the overall synergy or antagonism produced.

Using the assays above, therapeutic combinations of the present invention are determined to be useful HCV replication inhibitors.

Example 1

Combinations of VX-950 and polymerase inhibitors were tested in a checkerboard format in a 2-day Replicon assay with bDNA quantitation. The results are shown in Table 6. The combination of VX-950 and the polymerase inhibitor of formula I resulted in an additive to modestly synergistic effect. The combination of VX-950 and the polymerase inhibitor of formula II resulted in an additive to modestly synergistic effect. The combination of VX-950 and the polymerase inhibitor of formula III resulted in an additive effect.

TABLE 6

2-day Replicon Assay with bDNA quantitation

| Protease Inhibitor | Polymerase Inhibitor | Checkerboard Combo Result | VX-950 $IC_{50}$ | Polymerase Inhibitor $IC_{50}$ | Synergy | Log Volume |
|---|---|---|---|---|---|---|
| VX-950 | Formula I | Additive/Modest Synergy | 0.42 µM | 7.21 µM | 21.95 | 3.15 |
| VX-950 | Formula II | Additive/Modest Synergy | 0.34 µM | 1.04 µM | 45.13 | 6.48 |
| VX-950 | Formula III | Additive | 0.31 µM | 0.70 µM | 0.37 | 0.05 |

Example 2

The sensitivity of NS3 protease variants to ribavirin and interferon was assessed in a 2-Day HCV Replicon $IC_{50}$ Assay. The variants are as follows: at position 36, the wild-type valine was mutated to an alanine (V36A) or a methionine (V36M), the wild-type threonine at position 54 was mutated to an alanine (T54A), the wild-type arginine at position 155 was mutated to lysine (R155K), the wild-type arginine at position 155 was mutated to threonine (R155T) and the wild-type arginine at position 155 was mutated to methionine (R155M). As shown in Table 7, the results indicate the sensitivity of the variants to ribavirin and interferon. The fold change is the ratio of NS3 protease mutant IC50 to that of the Wild type IC50 for the same inhibitor. The sensitivity of replicons with the wild-type alanine at position 156 mutated to threonine (A156T) and the wild-type alanine at position 156 mutated to valine (A156V) is comparable to the wild-type (Lin, et al., 2005, supra).

TABLE 7

2-Day HCV Replicon $IC_{50}$ Assay of NS3 variants and ribavirin or interferon.

| Replicons | | Other Inhibitors | | | |
|---|---|---|---|---|---|
| | | IFN-α (units/ml) | | Ribavirin (μM) | |
| Protease domain | | Avg. $IC_{50}$ | Fold | Avg. $IC_{50}$ | Fold |
| Con1 Seq. | Changes | (uM) | Change | (uM) | Change |
| Wild Type (mADE) | — | 11.6 ± 1.1 | 1.0 | 57.8 ± 17.6 | 1.0 |
| Val 36 | V36M | 11.3 ± 5.9 | 1.0 | 32.9 ± 17.8 | 0.6 |
| | V36A | 10.3 ± 6.0 | 0.9 | 43.1 ± 21.3 | 0.7 |
| Arg 155 | R155K | 15.2 ± 12.3 | 1.3 | 37.2 ± 17 | 0.6 |
| | R155T | 4.8 ± 3.3 | 0.4 | 32.4 ± 17.7 | 0.6 |
| | R155M | 4.9 ± 1.0 | 0.4 | 38.9 ± 4.7 | 0.7 |
| Val 36/Arg 155 | V36M-R155K | 10.1 ± 5.9 | 0.9 | 40.6 ± 6.1 | 0.7 |
| | V36M-R155T | 3.1 ± 0.2 | 0.3 | 36.4 ± 1.3 | 0.6 |
| | V36A-R155K | 6.8 ± 0.5 | 0.6 | 35.8 ± 2.2 | 0.6 |
| | V36A-R155T | 3.9 ± 2.1 | 0.3 | 41.7 ± 21.6 | 0.7 |
| Thr 54 | T54A | 3.9 ± 0.5 | 0.3 | 21.7 ± 11.1 | 0.4 |

Example 3

The sensitivity of NS3 protease variants to VX-950 [Sarrazin, et al., "Dynamic Hepatitis C Virus Genotypic and Phenotypic Changes in Patients Treated With the Protease Inhibitor Telaprevir," Gastroenterology 132, pp. 1767-1777 (2007), which is incorporated herein by reference in its entirety] and the polymerase inhibitors of Formula I, II and III was assessed in a 2-Day HCV Replicon $IC_{50}$ Assay. The variants are as follows: at position 36, the wild-type valine was mutated to an alanine (V36A) or a methionine (V36M), the wild-type threonine at position 54 was mutated to an alanine (T54A), the wild-type arginine at position 155 was mutated to lysine (R155K), the wild-type alanine at position 156 was mutated to threonine (A156T) and the wild-type alanine at position 156 was mutated to valine (A156V). The variant, V36M+R155K, having two mutations was also tested. As shown in Table 8, the results indicate the sensitivity of the variants to VX-950 and to Formula I, II and III. The fold change is the ratio of NS3 protease mutant IC50 to that of the Wild type IC50 for the same inhibitor.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages and modifications are within the scope of the following claims.

What is claimed is:

1. A therapeutic combination comprising VX-950 and a polymerase inhibitor, wherein the polymerase inhibitor is any one of the compounds of formula (I) or (II)

(I)

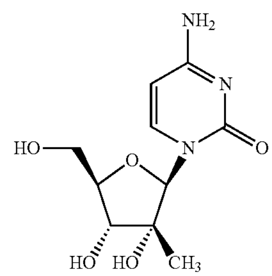

(II)

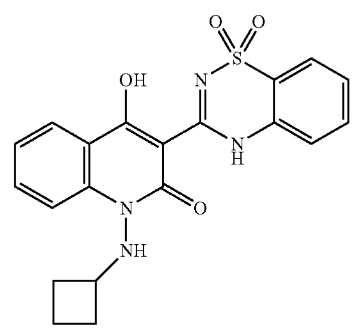

or a pharmaceutically acceptable salt thereof.

TABLE 8

2-Day HCV Replicon $IC_{50}$ Assay of NS3 variants and VX-950, Formula I, II and III

| Replicon | HCV Protease Inhibitor | | HCV Polymerase Inhibitors | | | | | |
|---|---|---|---|---|---|---|---|---|
| Protease | VX-950 | | Formula I | | Formula II | | Formula III | |
| Domain Changes | Avg. $IC_{50}$ ± STDEV | Fold Change | Avg. $IC_{50}$ ± STDEV | Fold Change | Avg. IC50 ± STDEV | Fold Change | Avg. $IC_{50}$ ± STDEV | Fold Change |
| Wild Type | 0.46 ± 0.101 | 1 ± 0.2 | 1.343 ± 0.473 | 1.0 | 0.347 ± 0.108 | 1.0 | 0.313 ± 0.032 | 1.0 |
| V36M | 3.38 ± 0.775 | 7.3 ± 1.7 | 1.589 ± 0.361 | 1.2 | 0.36 ± 0.164 | 1.0 | 0.227 ± 0.064 | 0.7 |
| V36A | 3.567 ± 1.05 | 7.7 ± 2.3 | 2.148 ± 0.874 | 1.6 | 0.571 ± 0.093 | 1.6 | 0.369 ± 0.066 | 1.2 |
| R155K | 3.587 ± 0.283 | 7.8 ± 0.6 | 2.371 ± 0.678 | 1.8 | 0.45 ± 0.023 | 1.3 | 0.39 ± 0.065 | 1.2 |
| V36M + R155K | 30.61 ± 0.637 | ≧65.2 | 2.716 ± 1.384 | 2.0 | 0.578 ± 0.331 | 1.7 | 0.419 ± 0.197 | 1.3 |
| T54A | 3.043 ± 0.819 | 6.6 ± 1.8 | 1.976 ± 0.388 | 1.5 | 0.564 ± 0.111 | 1.6 | 0.337 ± 0.045 | 1.1 |
| A156T | >30* | >65.2 | 1.27 ± 0.185 | 0.9 | 0.326 ± 0.003 | 0.9 | 0.306 ± 0.01 | 1.0 |
| A156V | >30* | >65.2 | 1.313 ± 0.216 | 1.0 | 0.264 ± 0.045 | 0.8 | 0.297 ± 0.066 | 0.9 |

2. A therapeutic combination comprising VX-950 and any one of the compounds of formula (I) or (II)

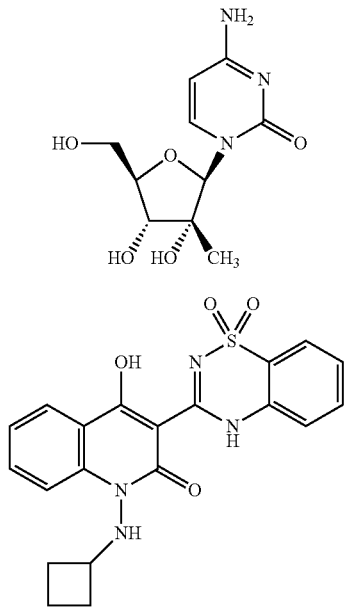

or a pharmaceutically acceptable salt thereof.

3. A kit comprising: (i) a therapeutic combination according to claim 1 or 2; and (ii) instructions for utilizing said combination.

4. A method of treating HCV infection or alleviating one or more symptoms thereof in a patient comprising the step of administering to the patient a therapeutic combination according to claim 1 or 2.

5. The method according to claim 4, wherein the HCV infection is genotype 1.

6. The method according to claim 4, wherein said patient is a treatment naive patient.

7. The method according to claim 4, wherein said patient is non-responsive to interferon monotherapy.

8. The method according to claim 4, wherein said patient is non-responsive to a combination therapy using ribavirin and an interferon.

9. A method of reducing HCV-RNA levels in a patient in need thereof, comprising the step of administering to said patient a therapeutic combination according to claims 1 or 2.

10. The method according to claim 9, wherein said HCV-RNA levels in a patient are reduced to a less than detectable level.

11. A pharmaceutical regimen, comprising administering to a patient in need thereof a therapeutic combination according to claim 1 or 2 until the HCV RNA level in the patient is below a detectable level.

12. A method of treating HCV infection or alleviating one or more symptoms thereof in a patient, comprising administering a therapeutic combination according to claim 1 or 2.

13. The method of claim 12, wherein the patient is infected by an HCV variant.

14. A method of eliminating or reducing HCV infection in a cell, comprising contacting the cell with a therapeutic combination according to claim 1 or 2.

15. The method of claim 14, wherein the cell contains an HCV variant.

* * * * *